United States Patent [19]

Gordon et al.

[11] 4,056,322

[45] Nov. 1, 1977

[54] PREPARATION OF ETHERS OF MONOSACCHARIDES

[75] Inventors: Paul Gordon; Bruce Ronsen, both of Chicago; Shrikant V. Kulkarni, Lombard, all of Ill.

[73] Assignee: Strategic Medical Research Corporation, Murray, Utah

[21] Appl. No.: 563,080

[22] Filed: Mar. 28, 1975

Related U.S. Application Data

[63] Continuation-in-part of Ser. No. 424,786, Dec. 14, 1973, Pat. No. 3,939,146, which is a continuation-in-part of Ser. No. 337,134, March 1, 1973, Pat. No. 3,939,145.

[51] Int. Cl.$^2$ .................. C07H 15/04; C07H 5/06
[52] U.S. Cl. ............................ 536/4; 424/180; 536/1; 536/18; 536/120
[58] Field of Search .............. 260/210 R; 536/1, 120, 536/18, 4

[56] References Cited

U.S. PATENT DOCUMENTS

| | | | |
|---|---|---|---|
| 2,715,121 | 8/1955 | Glen et al. | 260/210 R |
| 3,016,372 | 1/1962 | Krimmel | 260/210 R |
| 3,152,115 | 10/1964 | Morel et al. | 260/210 R |
| 3,157,634 | 11/1964 | Druey et al. | 260/210 R |
| 3,356,674 | 12/1967 | Ikeda et al. | 260/210 R |
| 3,419,544 | 12/1968 | Witzel et al. | 260/210 R |
| 3,862,121 | 1/1975 | Jaques et al. | 260/210 R |

*Primary Examiner*—Johnnie R. Brown
*Attorney, Agent, or Firm*—L. S. Van Landingham, Jr.

[57] ABSTRACT

Ethereally substituted monosaccharides are prepared from certain selectively derivatized monosaccharides. In practicing the method:

1. a monosaccharide derivative having the general formula $A_1$-O-H, wherein O is oxygen, H is hydrogen and $A_1$ is the residue of a monosaccharide selected from the group consisting of pentoses, hexoses and heptoses which has been derivatized with at least one substance selected from the group consisting of (1-a) at least one aliphatic alcohol containing 1–18 carbon atoms to produce an hydrolyzable acetal group at the site of at least one available hydroxyl residue, (1-b) at least one aldehyde containing 1–18 carbon atoms to produce at least one hydrolyzable acetal group at the site of at least one available hydroxyl residue, (1-c) at least one ketone containing 1–18 carbon atoms to produce at least one hydrolyzable ketal group at the site of at least one available hydroxyl residue, and (1-d) at least one organic acid residue containing 1–18 carbon atoms to produce an hydrolyzable ester group at the site of at least one available hydroxyl residue; is reacted with 2. an organic halide having the general formula Y - X, wherein X is selected from the group consisting of chlorine, bromine and iodine and Y is selected from the group consisting of (2-a) cyclic monovalent nitrogen containing organic radicals and residua, and (2-b) monovalent organic radicals and residue having the general formula -$R_1$B wherein B is selected from the group consisting of

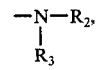

—O—$R_4$ and —S—$R_4$, $R_1$ is a divalent organic radical having a linear carbon chain length of about 1–7 carbon atoms, $R_2$ and $R_3$ are selected from the group consisting of —H, —OH, —SH, halogen and monovalent organic radicals and residua having a linear carbon chain length of about 1–7 carbon atoms, $R_4$ is selected from the group consisting of —H and monovalent organic radicals and residua having a linear carbon chain length of about 1–7 carbon atoms, N is nitrogen, O is oxygen, S is sulfur and H is hydrogen;

to produce an ethereally substituted monosaccharide derivative having the general formula A-O-Y wherein A, Y and O are as above defined. The monosaccharide derivative (1) and the organic halide (2) are reacted at an elevated reaction temperature while dissolved in a substantially anhydrous organic solvent in the presence of a solid substantially anhydrous strong inorganic base of a metal selected from the group consisting of the alkali metals and the alkaline earth metals. The resultant ethereally substituted monosaccharides may be partially or fully hydrolyzed in an aqueous acidic medium. In one preferred variant, 1,2:5,6-di-O-isopropylidene 3-O-3'-(N',N'-dimethylamino-n-propyl)-D-glucofuranose is prepared and, when desired, thereafter partially or fully hydrolyzed to produce 1,2-O-isopropylidene-3-O-3'-(N',N'-dimethylamino-n-propyl)-D-glucofuranose or 3-O-3'-(N'-N'-dimethylamino-n-propyl-D-glucose in the free amine and/or salt forms. The method is capable of preparing the ethereally substituted monosaccharides in high yield and purity with a minimum of side products. The resultant compounds exhibit striking antiviral activity and/or have other therapeutically valuable properties and are useful in the treatment of warm-blooded animals.

20 Claims, No Drawings

PREPARATION OF ETHERS OF MONOSACCHARIDES

RELATED APPLICATIONS

This application is a continuation-in-part of copending application Ser. No. 424,786, filed Dec. 14, 1973, now U.S. Pat. No. 3,939,146 for THERAPEUTIC COMPOSITION, NOVEL COMPOUNDS USEFUL THEREIN AND METHOD OF USING THE SAME. Application Ser. No. 424,786, in turn, is a continuation-in-part of copending application Ser. No. 337,134, now U.S. Pat. No. 3,939,145 filed Mar. 1, 1973 for THERAPEUTIC COMPOSITION, NOVEL COMPOUNDS USEFUL THEREIN AND METHOD OF USING THE SAME. The disclosures of applications Ser. Nos. 337,134 now U.S. Pat. No. 3,939,145 and 424,786 now U.S. Pat. No. 3,939,146 are incorporated herein by reference.

BACKGROUND OF THE INVENTION

The present invention relates to a novel method of preparing ethereally substituted monosaccharides from selectively derivatized monosaccharides. In a further variant, the invention is concerned with an improved method of partially or fully hydrolyzing the resultant ethereally substituted monosaccharide derivatives.

Copending U.S. applications Ser. Nos. 337,134 and 424,786 disclose and claim certain ethereal monosubstitutions of monosaccharides and monosaccharide derivatives. These compounds provide important biological signals which allow living cells to resist virus infections. The compounds are also useful in controlling other types of cell chemistry such as that involved in the formation of memory.

The aforementioned compounds cannot be conveniently synthesized in acceptable yield and in sufficiently high purity for pharmaceutical applications by the most widely accepted method for the synthesis of ethers, i.e., Williamson's synthesis. For instance, the Williamson synthesis has severe disadvantages in the preparation of 3-O- ethers of blocked monosaccharides such as 1,2:5,6-di-O-isopropylidene-D-glucose due in part to the stereochemical problems which are encountered. The only secondary hydroxyl group available in 1,2:5,6-di-O-isopropylidene-D-glucose is too sterically hindered to react at a practical rate with sodium metal to form the sodium salt. Additionally, the resultant sodium salt is almost insoluble in the solvents commonly used in the Williamson synthesis such as ethyl ether or benzene. The handling and preparation of the sodium metal required for synthesizing substantial quantities of 3-O- ethers of blocked monosaccharides and disposing of the excess sodium upon completing the reaction also constitute significant physical hazards.

The second stage of Williamson synthesis, which involves condensation of an alkyl halide with the sodium salt, is efficient and high yields are obtained. However, other problems arise when preparing the alkylamino ethers of monosaccharides. The alkylamino halide which is used in the condensation step must be in the form of the free amine and not as the corresponding mineral acid salt. Many of the amonoalkyl halides are volatile and very toxic when in the form of the free amine, but are not when present in the form of a mineral acid salt. An entirely satisfactory method of synthesizing 3-O- ethers of monosaccharides must therefore be capable of employing the aminoalkyl halide in the form of the mineral acid salt to avoid the inherent disadvantages of volatility and toxicity.

Still another method of condensing organic halides with blocked monosaccharides is disclosed in U.S. Pat. No. 2,715,121. This method involves autoclaving of the reaction mixture at high temperature under steam pressure and, when employed for the preparation of alkylamino ethers of monosaccharides, low yields of impure reaction products are obtained due to the preponderance of side reactions and the synthesis of side products. It is also very difficult to separate a desired substantially pure ether of monosaccharides from the reaction mixture which is sufficiently free of impurities for use in the therapeutic treatment treatment of warm-blooded animals.

In view of the foregoing, it is apparent that the art has long sought an entirely satisfactory method of preparing ethers of monosaccharides in high yield and purity which does not require hazardous chemicals or vigorous reaction conditions. However, such a method was not available prior to the present invention.

It is an object of the present invention to provide a novel method of preparing ethers of monosaccharides in high yield and purity.

It is a further object to provide a novel method of preparing ethers of monosaccharides wherein side reactions and side products are almost absent, and which requires mild reaction conditions and relatively nontoxic and nonhazardous reactants.

Still other objects and advantages of the invention will be apparent to those skilled in the art upon reference to the following detailed description and the examples.

THE DETAILED DESCRIPTION OF THE INVENTION INCLUDING PRESENTLY PREFERRED VARIANTS THEREOF

The method of the present invention for preparing an ethereally substituted monosaccharide comprises the step of reacting 1. a monosaccharide derivative having the general formula A-O-H, wherein O is oxygen, H is hydrogen and A is the residue of a monosaccharide selected from the group consisting of pentoses, hexoses and heptoses which has been derivatized with at least one substance selected from the group consisting of (1-a) at least one aliphatic alcohol containing 1–18 carbon atoms and preferably 1–4 carbon atoms to produce an acetal group at the site of at least one available hydroxyl residue, (1-b) at least one aldehyde containing 1–18 carbon atoms and preferably 1–4 carbon atoms to produce at least one acetal group at the site of at least one available hydroxyl residue, (1-c) at least one ketone containing 1–18 carbon atoms and preferably 1–4 carbon atoms to produce at least one ketal group at the site of at least one available hydroxyl residue, and (1-d) at least one organic acid residue containing 1–18 carbon atoms and preferably 1–4 carbon atoms to produce an ester group at the site of at least one available hydroxyl residue, with 2. an organic halide having the general formula Y — X, wherein X is selected from the group consisting of chlorine, bromine and iodine and Y is selected from the group consisting of (2-a) cyclic monovalent nitrogen containing organic radicals and residue, and (2-b) monovalent organic radicals and residua having the general formula —R₁—B, wherein B is selected from the group consisting of

—O—R₄ and —S—R₄, R₁ is a divalent organic radical having a linear carbon chain length of about 1–7 carbon atoms, R₂ and R₃ are selected from the group consisting of —H, —OH, —SH, halogen and monovalent organic radicals and residua having a linear carbon chain length of about 1–7 carbon atoms, R₄ is selected from the group consisting of -H and monovalent organic radicals and residua having a linear carbon chain length of about 1–7 carbon atoms, N is nitrogen, O is oxygen, S is sulfur and H is hydrogen, to produce an ethereally substituted monosaccharide derivative having the general formula A-O-Y wherein A and Y are as above defined. The monosaccharide derivative (1) and the said organic halide (2) are reacted at an elevated reaction temperature while dissolved in a substantially anhydrous organic solvent in the presence of a solid substantially anhydrous strong inorganic base of a metal selected from the group consisting of the alkali metals and the alkaline earth metals.

When R₂ or R₃ is halogen, the halogen may be F, Cl, Br or I, of which Cl or Br is usually preferred. The organic radical R₁, and R₂, R₃ and R₄ when they are organic radicals, may have branched or unbranched linear carbon chains and may be saturated or unsaturated, and when saturated, the linear and/or branched carbon chains may contain one or more double or triple carbon-to-carbon bonds. The linear and/or branched carbon chains of R₁, R₂, R₃ and R₄ may be substituted or unsubstituted and, when substituted, one or more substituents may be present, such as —OH, —SH, halogen (F, Cl, Br and/or I), branched or unbranched and saturated or unsaturated hydrocarbon radicals containing 1–7 and preferably 1–3 carbon atoms, —OR₅ and/or —SR₅ radicals wherein R₅ is a branched or unbranched and saturated or unsaturated hydrocarbon radical containing 1–7 and preferably 1–3 carbon atoms, carboxylic acid residua containing 1–7 and preferably 1–3 carbon atoms, and amino groups and aminohydrocarbon radicals containing 1–7 and preferably 1–3 carbon atoms. Preferably R₁ is a hydrocarbon radical having a linear carbon chain length of 1–3 or 1–4 carbon atoms and R₂, R₃ and R₄ are individually selected from the group consisting of hydrogen and/or hydrocarbon radicals having linear carbon chain lengths of 1–3 or 1–4 carbon atoms.

Examples of compounds from which the aforementioned cyclic radicals and residua are derived include (a) monovalent nitrogen containing saturated, unsaturated or aromatic carbocyclic compounds containing about 4–8 carbon atoms in the ring and preferably about 5–6 carbon atoms in the ring and at least one nitrogen atom attached thereto or to an organo substituent thereon, (b) heterocyclic organic compounds containing about 3–8 carbon atoms in the ring and at least one ring nitrogen atom and (c) derivatives of the foregoing compounds wherein at least one substituent is present, such as —OH, —SH, halogen (F, Cl, Br and/or I), branched or unbranched and saturated or unsaturated hydrocarbon radicals containing 1–7 and preferably 1–3 carbon atoms, —OR₆ and/or —SR₆ radicals, wherein R₆ is selected from branched or unbranched and saturated or unsaturated hydrocarbon radicals containing 1–7 and preferably 1–3 carbon atoms, carbocyclic acid residua containing 1–7 and preferably 1–3 carbon atoms, and amino groups and aminohydrocarbon radicals containing 1–7 and preferably 1–3 carbon atoms.

The derivatized monosaccharide residue A may exist in open chain or cyclic forms having, for example, the general formulae:

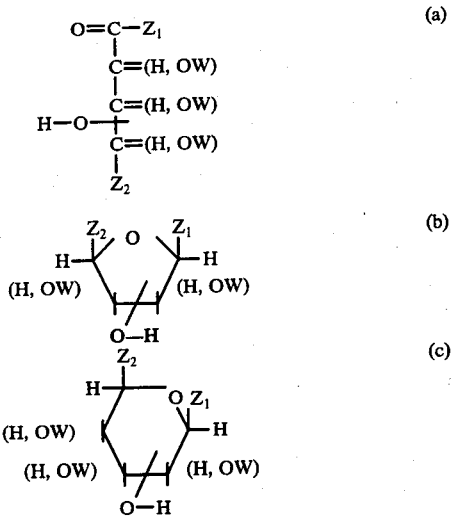

wherein Z₁ and Z₂ are selected from —H, —OH, and monovalent hydroxyalkyl, alkoxyl and/or alkoxyalkyl radicals containing up to about 3 carbon atoms, W is H or monovalent alkyl, alkenyl, cyclic alkane, cyclic aromatic or acyl radicals containing 1–18 carbon atoms and preferably 1–6 carbon atoms, or acyl containing 1–18 carbon atoms and preferably 1–4 carbon atoms, and at least one Z₁, Z₂ or W is other than —H or —OH. Preferably, all reactive -OH positions with the exception of the -OH position or positions to be ethereally substituted are derivatized and thus are other than —H or —OH. The above general formulae illustrate the various isomers of the pentoses, hexoses and heptoses, the relative spatial configuration of the —H and —OH groups about the ring and the derivatization thereof in accordance with one presently preferred variant of the invention. The hydroxyl or alkoxyl residue of the hemiacetal or hemiketal linkage may assume an α or a β configuration, and the derivatized monosaccharides may be in the form of anomers or mixtures of anomers.

The configurations of the various derivatives of isomers of the pentoses, hexoses and heptoses are well known to those skilled in this art and numerous reference books are available on the subject, the teachings of which are incorporated herein by reference. For example *Textbook of Biochemistry*, 4th Edition, by West et al (1966) and *The Monosaccharides* by Stanek, Cerny, Kocourek and Pacak (1963). The prior art discloses, for example, a total of eight open chain isomers for the reducing hexoses, and an even larger number of open chain isomers for the reducing heptoses. Either the D-series or the L-series of the pentoses, hexoses and heptoses may be used in practicing the invention, but it is usually preferred to use the D-series. The hexoses often give the best results and especially D-talose, D-galactose, L-galactose, D-idose, D-gulose, D-mannose, D-glucose, L-glucose, D-altrose and D-allose. The aforementioned pentoses, hexoses and heptoses may be derivatized at one or more of the hydroxyl groups and then ethreally substituted at any remaining available reactive position or positions. It is understood that the ethereal substitution of certain available reactive positions of specific monosaccharide derivatives results in more therapeutically active or less toxic compounds. For instance, the ethereal substitution of the 3-O- position of 1,2-O-isopropylidene-D-glucofuranose or 1,2:5,6-di-O-isopropyliene-D-glucofuranose and the 6-O- position of 1,2-O-isopropylidene-D-galactopyranose or 1,2:3,4-di-O-isopropylidene-D-galactopyranose results in especially valuable compounds.

The following substituents, i.e., Y in the aforementioned general formula A-O-Y may be ethereally substituted employing an organic halide reactant of the aforementioned formula Y — X, on any of the available reactive positions of the various isomers of the derivatized pentoses, hexoses and heptoses, to produce nontoxic compounds having exceptional therapeutic activity:
  -(n-propylamino),
  -(N',N'-dimethylamino-n-propyl),
  -(N',N'-dimethylaminoisopropyl),
  -(N'-methylpiperidyl),
  -(N',N'-dimethylaminoethyl),
  -(N',N'-diethylaminoethyl),
  -(2',N',N'-trimethylamino-n-propyl),
  -dimethylamino,
  -(N',N'-dimethylaminomethyl),
  -(N',N'-dimethylaminopropyl),
  -(N',N'-dimethylamino-iso-butyl),
  -(N',N'-dimethylamino-n-butyl),
  -(N',N'-dimethylamino-iso-pentyl),
  -(N',N'-dimethylaminopentyl),
  -(N'-methylamino-n-propyl),
  -(N'-methyl-N'-ethylamino-n-propyl),
  -(N',N'-diethylamino-n-propyl),
  -(amino-n-propyl),
  -(N'-ethylamino-n-propyl),
  -(N'-propylamino-n-propyl),
  -(N',N'-iso-propylamino-n-propyl),
  -(1',2'-ethylimino-n-propyl),
  -(1'-n-propylpyrrolidyl),
  -(1'-n-propylpiperidyl),
  -piperidyl, and
  -(N',N'-dimethylamino-sec-butyl). Of the foregoing, -(N',N'-dimethylamino-n-propyl) is presently preferred as Y in the formulae Y — X and A-O-Y and especially when substituted in the available 3-O-position of 1,2-O-isopropylidene-D-glucofuranose or 1,2:5,6-di-O-isopropylidene-D-glucofuranose or the 6-O- position of 1,2-O-isopropylidene-D-galactopyranose or 1,2:3,4-di-O-isopropylidene-D-galactopyranose.

The following compounds of the aforementioned general formula A-O-Y have exceptional wide spectrum antiviral activity and other therapeutically valuable properties, and may be prepared by the method of the invention when employing as reactants the corresponding monosaccharide derivatives A-O-H (or hydrolyzable precursors thereof) and organic halides Y — X:

3-O-3'-(n-propylamino)-1,2-O-isopropylidene-D-glucofuranose,
3-O-3'-(N',N'-dimethylamino-n-propyl)-1,2-O-isopropylidene,D-glucofuranose,
3O-4'-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-2'-(N',N'-diethylaminoethyl)-1,2-O-isopropylidene-D-glucofuranose,
3-O-3'-(2',N',N'-trimethylamino-n-propyl)-1,2-O-isopropylidene-D-glucofuranose,
3-O-2'-(N',N'-dimethylaminopropyl)-1,2:5,6-di-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1,2-O-isopropylidene-D-galactopyranose,
6-O-2'-(N',N'-dimethylaminopropyl)-1,2-O-isopropylidene-D-galactopyranose,
3-O-3'-(n-propylamino)-1,2:5,6-di-O-isopropylidene-D-glucofuranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-"-(N',N'-dimethylaminoethyl)-1,2:5,6-di-O-isopropylidene-D-glucofuranose,
3-O-2'-(N',N'-diethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofuranoside, and organic and inorganic acid salts thereof.

Additional compounds of the general formula A-O-Y, wherein Y is

which may be prepared by the method of the invention when employing as reactants the corresponding monosaccharide derivatives A-O-H(or hydrolyzable precursors thereof) and organic halides Y — X are listed below:

| Monosaccharide Residue (A)* | Substituent (Y) | | |
|---|---|---|---|
| | $R_1$ | $R_2$ | $R_3$ |
| 3-O-1,2-O-isopropylidene-D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O-1,2-O-isopropylidene-D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |
| 3-O-1,2:5,6-di-O-isopropylidene-D-gluco furanose | 3'-n-propyl | H | methyl |
| " | " | ethyl | " |

-continued

| Monosaccharide Residue (A)* | Substituent (Y) | | |
|---|---|---|---|
| | R₁ | R₂ | R₃ |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O-1,2:3,4-di-O-iso-propylidene-D-galactopyrinose | | | |
| " | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |

*A or a hydrolyzable precurser thereof

Still other compounds of the general formula A-O-Y wherein Y is a cyclic monovalent nitrogen-containing organic radical or residue, which may be prepared by the method of the invention when employing as reactants the corresponding monosaccharide derivatives A-O-H (or hydrolyzable precursors thereof) and organic halides Y — X are as follows:

| Monosaccharide Residue (A)* | Substituent (Y) | |
|---|---|---|
| | Cyclic Radical | Substituent on the Cyclic Radical |
| 3-O-1,2-O-isopropylidene-D-glucofuranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |
| 6-O-1,2-O-isopropylidene-D-galactopyranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |
| 3-O-1,2:5,6-di-O-iso-propylidene-D-glucofuranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |
| 6-O-1,2:3,4-di-O-iso-propylidene-D-galactopyranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |

*A or a hydrolyzable precursor thereof.

The method of the present invention also provides certain novel compounds of the general formula A-O-Y which may be prepared when employing as reactants the corresponding monosaccharide derivatives A-O-H (or hydrolyzable precursors thereof) and the corresponding organic halides Y — X, as follows:

3-O-2'-(N',N'-dimethylaminoethyl)-1,2-O-isopropylideneglucofuranose,

3-O-3'-(2',N',N'-trimethylamino-n-propyl)-1,2-O-isopropylideneglucofuranose,

3-O-2'-(N',N'-dimethylaminopropyl)-1,2-O-isopropylideneglucofuranose,

6-O-3'-(N',N'-dimethylamino-n-propyl)-1,2-O-isopropylidenegalactopyranose,

6-O-2'-(N',N'-dimethylaminopropyl)-1,2-O-isopropylidenegalactopyranose,

3-O-3'-(N',N'-dimethylamino-n-propyl)-1,2:5,6-di-O-isopropylideneglucofuranose,

3-O-4'-(N'-methylpiperidyl)-1,2:5,6-di-O-isopropylideneglucofuranose,

3-O-2'-(N',N'-dimethylaminoethyl)-1,2:5,6-di-O-isopropylideneglucofuranose,

3-O-3'-(2',N',N'-trimethylamino-n-propyl)-1,2:5,6-di-O-isopropylideneglucofuranose, 3-O-2'-(N',N'-dimethylaminopropyl)-1,2:5,6-di-O-isopropylideneglucofuranose, 6-O-3'-(N',N'-dimethylamino-n-propyl)-1,2:3,4-di O-isopropylidenegalactopyranose, 6-O-2'-(N',N'-dimethylaminopropyl)-1,2:3,4-di-O-isopropylidenegalactopyranose, α-N',N'-dimethylamino-iso-propyl-2,3:5,6-di-O-isopropylideneglucofuranoside, and organic and inorganic acid salts thereof.

The dextrorotatory or levorotatory species of the foregoing novel compounds may be prepared by the method of the invention by selecting as reactants the corresponding dextrorotatory or levorotatory monosaccharide derivatives A-O-H (or hydrolyzable precursors thereof), respectively, and the corresponding organic halides Y — X.

When the organic halide is an amine, it is preferred to use the organic acid or inorganic acid salt thereof rather than the free amine, and especially when the free amine is volatile and/or toxic. Thus, the method of the present invention is capable of using a non-volatile and/or non-toxic form of the organic halide as a reactant. This eliminates the hazards normally associated with Williamson's synthesis or similar reactions of this type.

The monosaccharide derivative is condensed with the organic halide in the presence of a solid substantially anhydrous strong inorganic base of the alkali metals and/or the alkaline earth metals. The preferred alkali metals are sodium and potassium, and the preferred alkaline earth metal is calcium. The inorganic base may be, for example, in the form of an oxide or hydroxide of the alkali metal and/or the alkaline earth metal. The hydroxides are preferred and substantially anhydrous sodium hydroxide usually produces the best results. Still better results are obtained when the inorganic base has been heated to an elevated temperature to remove moisture, carbon dioxide, or other absorbed substances and thereby regenerate a fresh surface. The temperature of heating preferably should exceed 100° C and may be as high as is necessary to remove the moisture and carbon dioxide and regenerate a fresh surface provided the temperature does not exceed the melting point of the inorganic base. Similarly, the period of heating should be sufficiently long in duration to remove the deleterious moisture and/or carbon dioxide and to regenerate a fresh surface on the inorganic base. Extended heating normally does not have an adverse effect once the moisture and carbon dioxide are removed. In most instances, the inorganic base may be heated at a temperature of approximately 100°–200° C for about 6-48 hours, and preferably at about 160° C for approximately 12–24 hours prior to use. It is also advantageous for the inorganic base to be in particulate form, such as in the form of pellets, flakes, beads, or other small shapes. The resultant extended surface area seems to aid in promoting the reaction. The size of the particles may vary over wide ranges as it is only necessary that sufficient surface area be presented to promote the reaction. The inorganic base may be, for example, in the form of small thin sodium hydroxide flakes or 40 mesh sodium hydroxide beads. However, flakes, beads or particles several times smaller or larger than this may be employed, such as 1-5 times smaller or larger. Powdered or pulverized inorganic bases and especially finely powdered or pulverized sodium hydroxide may be used so as to provide a very high surface area per unit weight.

The inorganic base should be present in an amount of at least 1 chemical equivalent for each mole of the organic halide reactant in instances where the organic halide is not an amine salt. In the latter instance, the inorganic base should be present in an amount of at least 2 chemical equivalents for each mole of the organic halide so as to be capable of reacting with the organic or inorganic acid forming the amine salt and to provide sufficient excess inorganic base to react with the halide that is released upon reaction of the organic halide with the monosaccharide derivative. Much larger quantities of the inorganic base than these minimum amounts may be employed, such as 2-10 or more times the theoretical quantities required for the aforementioned reactions.

The monosaccharide derivative and the organic halide are reacted at an elevated reaction temperature while dissolved in a substantially anhydrous organic solvent. Any suitable substantially anhydrous organic solvent which is inert under the reaction conditions with respect to the reactions and the inorganic base may be employed. Examples of such organic solvents include cyclic and open chain ethers containing about 4-8 carbon atoms such as 1,4-dioxane and tetrahydrofuran and ethyl ether, and hydrocarbons, halogenated hydrocarbons and ketones containing about 2-10 carbon atoms such as benzene, hexane, carbon tetrachloride and acetone. The preferred solvents are 1,4-dioxane and tetrahydrofuran, of which 1,4-dioxane produces exceptional results. The reactants and the desired reaction product should be soluble in the selected solvent and the solvent should be present in an amount sufficient to dissolve the reactants and the reaction product. Much larger quantities of solvent may be used such as 1-10 or more times the minimum quantity necessary to effect dissolution of the reactants and the desired reaction product.

The reaction time and temperature may vary over wide ranges. It is only necessary to employ sufficiently elevated temperature conditions to effect reaction between the derivatized monosaccharide and the organic halide without substantial thermal decomposition, and to allow the reaction to proceed for a sufficiently long period of time to reach a desired degree of conversion. The reaction temperature may be, for example, about 30°-150° C and is preferably about 60°-120° C. Usually the best results are achieved at a reaction temperature of approximately 95°-105° C. The reflux temperatures of 1,4-dioxane, tetrahydrofuran, acetone, ethyl ether and carbon tetrachloride are very satisfactory. When desired, the reaction may proceed under superatmospheric pressure to allow higher reaction temperatures to be employed and especially when using low boiling solvents such as ethyl ether. Atmospheric moisture and/or other extraneous sources of water should not be allowed to contaminate the reaction mixture for best results.

The reaction is preferably carried out in the presence of a scavenger for water which is inert under the reaction conditions. Any suitable inert scavenger for water may be employed such as anhydrous calcium chloride, anhydrous sodium sulfate and the like. Anhydrous calcium chloride is usually preferred. The scavenger is preferably present in an amount sufficient to scavenge the water of reaction and/or any additional water which inadvertently enters the reaction mixture. Much larger quantities may be present such as 1-10 or more times the aforementioned minimun quantity.

The reaction of the derivatized monosaccharide with the organic halide is allowed to proceed for a sufficiently long period of time to result in the desired percent conversion. As a general rule, it is preferred that the conversion be more than 75% complete and preferably more than 90% complete. The progress of the reaction may be conveniently monitored by gas chromatographic analysis and, in such instances, the reaction may be terminated at the desired percent conversion.

When the reaction is completed, the reaction mixture is filtered to remove the solid residue which is largely the inorganic base and the scavenging agent. The filtration step should be conducted in a non-oxidizing atmosphere and out of contact with an oxidizing gas such as air unless the reaction mixture has first been cooled to a sufficiently low temperature to prevent oxidation. It is usually preferred that the hot reaction mixture be filtered under an atmosphere of an inert gas such as nitrogen, argon or helium directly into a distillation flask using a filter candle or other suitable filtration means to prevent contact with atmospheric air. The solid filter residue may be discarded and the various components in the filtrate may be separated by distillation under reduced pressure. Preferably, the solvent has a boiling point lower than the reactants and the desired reaction product and, in such instances, the solvent fraction is recovered first. Upon drying with a dessicant such as anhydrous calcium chloride, the recovered solvent may be reused. After removal of the solvent fraction, usually the unreacted organic halide fraction distills over followed by an azeotropic mixture of the unreacted derivatized monosaccharide and the desired product. The azeotropic mixture is followed by distillation of a final fraction which is the desired product, i.e., the etherally substituted monosaccharide.

While the foregoing sequence of steps are preferred in processing the reaction mixture to recover the desired ethereally substituted monosaccharide product, it is understood that other suitable conventional processing techniques may be employed. However, the aforementioned steps have been found to be very satisfactory in obtaining the desired product in high yield and in very high purity. Inasmuch as the products of the invention are useful as therapeutic agents, high purity is especially important as potentially harmful side products and other impurities must be kept at a minimum.

In a further variant of the invention, an hydrolyzable monosaccharide derivative is selected for reaction with the organic halide which has the general formula $A_1$-O-H wherein O is oxygen, H is hydrogen and $A_1$ is the residue of a monosaccharide selected from the group consisting of pentoses, hexoses and heptoses which has been derivatized with at least one substance selected from the group consisting of (1-a) at least one aliphatic alcohol containing 1-18 carbon atoms to produce a hydrolyzable acetal group at the site of at least one available hydroxyl residue, (1-b) at least one aldehyde containing 1-18 carbon atoms to produce at least one hydrolyzable acetal group at the site of at least one available hydroxyl residue, (1-c) at least one ketone containing 1-18 carbon atoms to produce at least one hydrolyzable ketal group at the site of at least one available hydroxyl residue, and (1-d) at least one organic acid residue containing 1-18 carbon atoms to produce an hydrolyzable ester group at the site of at least one available hydroxyl residue. The resultant reaction produces an etherally substituted monosaccharide derivative having the general formula $A_1$-O-Y, wherein $A_1$ and O are as above defined and Y is as defined hereinbefore for the organic halide Y − X. In such instances, $A_1$ may be thought of as being an hydrolyzable precurser of A as defined hereinbefore in the compound A-O-Y. The derivatized hydrolyzable monosaccharides $A_1$-O-H may be reacted with the organic halide under the same conditions and following the same procedures as mentioned hereinbefore when preparing the compound having the general formula A-O-Y.

The etherally substituted monosaccharide derivative having the general formula $A_1$-O-Y may be recovered from the reaction mixture by the steps set out above for recovering the compound A-O-Y. Thereafter, at least one of the hydrolyzable acetal, ketal and/or ester groups is removed from $A_1$ by hydrolysis in an acidic aqueous medium having a pH value less than 7 to produce an ethereally substituted monosaccharide having the general formula $A_2$-O-Y, wherein O and Y are as above defined and $A_2$ is the residue of a monosaccharide corresponding to $A_1$ as above defined with at least one of the said acetal, ketal and/or ester groups being removed therefrom. In instances where the acidic aqueous medium has a pH value of about 3-6 and preferably about 4.0-4.5, it is possible to remove only a portion of the said acetal, ketal and/or ester groups. When the pH value is less than 3, such as about 1-2.5, when desired it is possible to remove all of the acetal, ketal and ester groups from the derivatized -OH positions. The aqueous medium which is used for the hydrolysis step may be adjusted in pH value by addition of any suitable organic and/or inorganic acid which will result in the desired pH value. Mineral acids such as sulfuric acid and hydrochloric acid are usually preferred. In instances where the organic halide is an amine, the resulting hydrolyzed or partially hydrolyzed product is recovered as the mineral acid salt by lyophilization. The recovered product may be recrystallized from a suitable organic solvent such as methanol to obtain the final pure product. The acidic aqueous medium for the hydrolysis step should be substantially non-oxidizing with respect to the desired product as oxidized impurities may be formed.

The hydrolysis step is conducted at an elevated temperature and for a sufficiently long period of time to effect the desired degree of hydrolysis. For instance, the hydrolysis step may be conducted at the reflux temperature of the acidic aqueous medium for a period of approximately 6-48 hours, and preferably for about 12-24 hours or until completion of the desired degree of hydrolysis as indicated by monitoring the progress of the reaction by gas chromatographic analysis. In the latter instance, the hydrolysis is terminated when the analytical data indicate the disappearance of a peak due to the starting compound and the appearance of new peak which is indicative of the desired hydrolysis product. Thereafter, the aqueous solution may be cooled and the pH value adjusted to above 6.0, and preferably to about 6.5, and lyophilized. The resultant desired hydrolysis product is precipitated and recovered in the form of crystals which may be purified by recrystalization from organic solvents as aforementioned.

It is understood that the preparation of simple derivatives of the compounds described herein is embraced by the method of the invention. Such derivatives may be prepared by prior art techniques and procedures. For example, the free amine compounds are basic and form organic acid salts and inorganic acid salts. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, acetic acid, alkylcarboxylic acids, oxalic acid, tartaric acid, lactic acid, pyruvic acid, malic acid, succinic acid, gluconic acid and glucuronic acid. The aqueous solution of the resulting salt may be evaporated to the volume necessary to assure precipitation of the salt upon cooling. The precipitated salt is recovered by filtration, washed and dried to obtain a final amine salt product. The amine salts are often preferred for use in formulating the therapeutic compositions as they are crystalline and relatively nonhygroscopic. The amine salts are also better adapted for intramuscular injection than are the free amines.

Prior art blocking techniques may be employed for derivatizing the monosaccharide to be reacted with the organic halide such as acetonization and acetylation. Suitable prior art blocking methods are described in U.S. Pat. No. 2,715,121 and in the specific examples appearing hereinafter. In instances where an aldehyde or ketone is reacted with hydroxyl groups on adjacent carbon atoms, the initial compound may be dissolved in the desired aldehyde or ketone under anhydrous conditions and a Lewis acid catalyst may be added in a catalytic quantity, such as 1% zinc chloride or anhydrous phosphoric acid. Often acetone is the preferred blocking agent, but aldehydes or ketones of much higher molecular weight may be used when desired such as those containing up to 25 carbon atoms. The reaction mixture may be agitated at room temperature for a prolonged reaction period such as 24-48 hours. The compound may be blocked in a plurality of positions, such as the 1,2- and/or 5,6- positions.

It is also possible to block one or more free hydroxyl positions of the compounds with an ester group, wherein the carboxylic acid dresidue contains 1-18 and preferably 1-3 carbon atoms. The ester derivatives likewise may be prepared following prior art techniques such as by reacting a carboxylic acid anhydride with the compound following prior art practices. Additionally, the α or β alkyl derivatives of monosaccharide derivatives such as 2,3:5,6-di-O-isopropylidene-D-glucofuranoside may be prepared following prior art techniques. In this latter instance, the compound is dissolved in a dry alcohol having the desired carbon chain length with aforementiond residua and reacted with the compound in the presence of a catalyst such as the hydrogen chloride of Dowex 50 H+ resin. While the above discussed derivatives are presently preferred, it is understood that still other simple derivatives may be prepared following prior art techniques and then used in practicing the present invention. In addition to the foregoing, the compounds may also include monosubstitutions of monosaccharide derivatives in which the substrate Y may be replaced by a substitutent $R_8$ wherein $R_8$ is a deoxymonosaccharide derivative of halogen, keto, amino, lower alkyl, mercapto, alkenyl, alkynyl, aromatic, heterocyclic or alkylcarboxylic acid and its derivatives. $R_8$ may also represent the same groups as the above substrate of the monosaccharide derivative ethers. Still other compounds have a general formula A-O-Y wherein Y is -$R_9$-S-$R_{10}$, where $R_9$ is a saturated or unsaturated hydrocarbon radical containing 1–7 carbon atoms and $R_{10}$ is a monovalent saturated or unsaturated hydrocarbon radical containing 1–7 carbon atoms and hydrogen.

The compounds prepared by the method of the invention are especially useful as wide spectrum antiviral agents for the therapeutic treatment of warm-blooded animals. They exhibit potent antiviral activity against both RNA and DNA viruses, contrary to the prior art antiviral agents. The compounds exhibit marked suppression of virus particle multiplication and virus induced cell injury in animal and human cell tissue culture systems against such widely varying viruses as herpes simplex, influenza A, mumps, poliovirus and rhinovirus.

The following specific examples further illustrate the present invention.

EXAMPLE 1

To a solution of 104 g (0.4 mole) of 1,2:5,6-di-O-isopropylidene-D-glucofuranose in 550 ml of 1,4-dioxane was added 189.7 g (1.2 mole) of 3-chloro-N,N-dimethylamino propane in the form of the hydrochloride salt and 144 g (3.6 mole) of sodium hydroxide. The suspension was mechanically stirred and heated to reflux for 18 hours. The reaction mixture thus prepared was filtered the solids were washed with 1,4-dioxane and the washings were combined with the filtered liquid. The solvent was removed under reduced pressure and an amber-colored viscous oil was obtained.

The oil was distilled under high vacuum (less than 1 mm Hg) while using a very slight dry nitrogen purge to obtain high and low boiling fractions. The low boiling fraction was identified as unreacted 3-chloro-N,N-dimethylamino propane. The high boiling fraction had a boiling point of 148°–154° C at 2.5 mm Hg and was a clear viscous oil with an optical rotation of $\{\alpha\}_D^{25} = -19.3°$ neat (100 mm) and a density of 0.95 g/cc. The refractive index was $\eta_D^{26} = 1.4576$. Gas chromatography showed a purity greater than 99%. An elemental analysis showed: C, 59.13; H, 8.99; N, 4.12; O, 27.7. The yield was 80% of the novel compound 1,2:5,6-di-O-isopropylidene-3-O-3'-(N',N'-dimethylamino-n-propyl)-D-glucofuranose.

A portion of the above oil (10 g) was hydrolyzed in aqueous sulfuric acid at a pH value of 1.9–2.1 for 10 hours with refluxing. The resulting solution was adjusted to a pH value of 4.5 with saturated Ba(OH)$_2$ solution, centrifuged, and filtered through an ultrafine filter. The filtrate was lyophillized to a white-to-slightly yellow solid having a melting point of 78°–80° C. Gas chromatography data indicated above 99% purity of the novel compound 3-O-3'-(N',N'-dimethylamino-n-propyl)-D-glucopyranose. In thin-layer chromatography, the flow rate on silica gel with a solvent mixture composed of n-propanol, ethyl acetate, H$_2$O and NH$_3$ in the ratio by volume of 60:10:30:10, respectively, was $R_f = 0.356$.

A portion of the oil is partially hydrolyzed to 1,2-O-isopropylidene-3-O-3'-(N',N'-dimethylamino-n-propyl)-D-glucofuranose by dissolving it in distilled water and adjusting the pH of the approximately 1M solution to 3.0 ± 0.2 with 6N HCl. The solution is extracted twice with chloroform and the clear aqueous solution is refluxed for about 2 hours. Completion of partial hydrolysis reaction was monitored by gas chromatography from disappearance of the peak of parent compound and appearance of a new peak with larger retention time. The solution is then cooled, made alkaline with 30% sodium hydroxide to pH 10.5 and then extracted with chloroform. The chloroform phase is separated, dried over anhydrous magnesium sulfate and vacuum distilled to remove the solvent. The resulting colorless viscous oil has optical rotation of $\alpha_{neat}° = -12°$ and refractive index of 1.4687 at 25° C. Alternatively, the compound can be obtained as hydrochloride salt by lyophillizing the aqueous solution after partial hydrolysis at pH 4.0–4.5. A white crystalline material is obtained which is recrystallized from methanol. The crystalline hydrochloride of 1,2-O-isopropylidene-3-O-3'-(N',N'-dimethylamino-n-propyl)-D-glucofuranose has a melting point of 181°–183° C and purity as indicated by gas chromatography is 98+%. Infrared spectrophotometry indicates presence of strong -OH band which is not present in parent oil. The elemental analysis for the hydrochloride salt in a typical batch showed: C, 49.09; H, 8.40; N, 4.14; Cl, 10.32; O, 28.12. Theoretical values are as follows: C, 49.19; H, 8.19; N, 4.09; Cl, 10.39; O, 28.11.

The gas-liquid chromatograms for the above intermediate and final novel compounds were run on a Beckman GC, Model 72-5 with a hydrogen flame detector. The column used for the intermediate novel compound was a commercially available SE-52 column, wherein methyl phenyl resins act as stationary phases supported on Chromosorb W (H.P.) which is made by Johns-Manville Corporation. The final novel compound was chromatographed on a Chromosorb 103 glass column, which is packed with porous resins. The foregoing materials are commercially available.

EXAMPLE 2

Starting with 51 g (0.3 mole) of 4-chloro-N-methylpiperidine hydrochloride and 26 g (0.1 mole) of 1,2:5,6-di-O-isopropylidene-D-glucofuranose and 36 g of NaOH in 150 ml 1,4-dioxane, condensation was accomplished using the general procedure outlined in Example 1. The residue remaining following vacuum distillation was dissolved and recrystallized from hot methanol. The melting point was 106°–107.5° C (sharp).

Hydrolysis of the above product is H$_2$SO$_4$ at a pH value of 2.1 yielded 3-O-4'-(N'-methylpiperidyl)-D-glucopyranose having an optical rotation of $\{\alpha\}_D^{25} = +38.42°$ in H$_2$O. A gas chromatography analysis in accordance with Example 1 indicated that the purity of the product was in excess of 96%. The melting point was 62°–65° C.

EXAMPLE 3

A solution of 0.1 mole of 1,2:5,6-di-O-isopropylidene-D-glucofuranose in 50 ml of tetrahydrofuran was added to a suspension of 0.3 mole of 2-chloro-N,N-diethylaminoethane hydrochloride and 36 g of sodium hydroxide in 100 ml of tetrahydrofuran. The suspension was mechanically stirred and refluxed overnight and the reaction mixture was treated as set out in Example 1. The desired product, 1,2:5,6-di-O-isopropylidene-3-O-2'-(N',N'-diethylaminoethyl)-D-glucofuranose was obtained as a clear yellow liquid (boiling point 144°–150°

C/0.15 mm Hg) having an optical rotation of $\{\alpha\}_D^{28} = -20.6°$ neat and a refractive index of $\eta_D^{25} = 1.4532$. The liquid solidified on exposure to air, probably due to formation of the carbonate salt. The yield was 85%.

Ten grams of the above product were hydrolyzed with aqueous sulfuric acid at a pH value of 1.9–2.1 for ten hours under reflux. The resulting solution was adjusted to a pH value of 4–5 with saturated barium hydroxide solution and then centrifuged and filtered. Lyophillization of the filtrate yielded 6.55 g of light brown crystalline 3-O-2'-(N',N'-diethylaminoethyl)-D-glucopyranose. The optical rotation in water was $\{\alpha\}_D^{25} = +36.33°$. A gas chromatography analysis in accordance with Example 1 indicated that the purity was in excess of 99%.

EXAMPLE 4

To 26 g (0.1 mole) of 1,2:5,6-di-O-isopropylidene-D-glucofuranose and 36 g (0.9 mole) of sodium hydroxide in 150 ml of refluxing tetrahydrofuran was added dropwise over one hour 0.3 mole of 3-bromopropionitrile in 50 ml of tetrahydrofuran. The reaction mixture was refluxed for an additional six hours and then filtered. The solids were washed with tetrahydrofuran and the washings were combined with the filtrate. The solvent was removed under reduced pressure and solid 1,2:5,6-di-O-isopropylidene-3-O-3'-propionitrile-D-glucofuranose was obtained. The decomposition point was 165° C and it was light sensitive indicating utility in photographic applications.

Five grams (0.016 mole) of the above product was dissolved in anhydrous ether and added dropwise to a suspension of 0.76 g (0.02 mole) of lithium aluminum hydride in ether. The resulting complex was dissolved in cold hydrochloric acid and neutralized rapidly with sodium bicarbonate. The suspension thus produced was extracted with chloroform and the solvent was removed to obtain a yellow oil in a yield of 250 mg. Gas chromatography in accordance with Example 1 indicated a purity of 98% and there was a sharp infrared band at 3400 cm$^{-1}$. The oil was hydrolyzed at a pH value of 2.1 in sulfuric acid and lyophillized to dryness. The yield was 85 mg of 3-O-3'-(n-propylamino)-D-glucopyranose.

EXAMPLE 5

The 3-O-2'-(N',N'-dimethylaminopropyl) derivative of 1,2:5,6-di-O-isopropylidene-D-glucofuranose was prepared by condensing 0.1 mole of 1,2:5,6-di-O-isopropylidene-D-glucofuranose with 0.3 mole of 2-chloro-N,N-dimethylamino propane hydrochloride in the presence of 0.9 mole of sodium hydroxide in 150 ml of 1,4-dioxane. The reaction mixture was fractionally distilled under reduced pressure to obtain a yellow viscous oil (boiling point 142°–145° C/0.07 mm Hg) in 81% yield. The optical rotation was $\{\alpha\}_D^{25} = -21.5°$ neat and the refractive index was $\eta_D^{25} = 1.4549$. Gas chromatography in accordance with Example 1 indicated only one component.

The above prepared yellow viscous oil (10 g) was hydrolyzed with aqueous sulfuric acid at a pH value of 2.0 by refluxing for 10 hours. The pH value of the hydrolysate was adjusted to 4–5 with saturated barium hydroxide solution, filtered and lyophillized to obtain 10.5 g of light yellow crystals of 3-O-2'-(N',N'-dimethylaminopropyl)-D-glucopyranose. The optical rotation in water was $\{\alpha\}_D^{25} = +37.86°$. Gas chromatography in accordance with Example 1 indicated a purity in excess of 82%.

A portion of the oil, 1,2:5,6-di-O-isopropylidene-3-O-2'-(N',N'-dimethylaminopropyl)-D-glucofuranose, is partially hydrolyzed at pH 3.0 ± 0.2 as indicated in Example 1. A white crystalline hydrochloride salt is obtained on lyophillization. The salt obtained is highly hygroscopic, with gas chromatographic purity being of the order of 80%.

EXAMPLE 6

To 0.2 mole of 1,2:5,6-di-O-isopropylidene-D-glucofuranose was added 0.3 mole of 2,N,N-trimethylaminopropyl chloride hydrochloride along with 36 g of sodium hydroxide. The general reaction procedure was in accordance with Example 1. The oil resulting from the reaction had a boiling point of 144°–146° C at 0.6 mm Hg and an optical rotation of $\{\alpha\}_D^{20} = -20.05°$ neat.

The above product was hydrolyzed according to the general method outlined in Example 1 to obtain the desired 3-O-3'-(2',N',N'-trimethylamino-n-propyl)-D-glucopyranose. The optical rotation of the product in water was $\{\alpha\}_D^{20} = +38.0°$.

A portion of the oil, 1,2:5,6-di-O-isopropylidene-3-O-3'-(2',N',N'-trimethylamino-n-propyl)-D-glucofuranose, is partially hydrolyzed at pH 3.0 ± 0.2 according to the procedure mentioned in Example 1. A white crystalline 1,2-O-isopropylidene-3-O-3'-(2',N',N'-trimethylamino-n-propyl)-D-glucofuranose hydrochloride was obtained which is highly hygroscopic in nature. Optical rotation of the hydrochloride salt at pH 7.0 and 25° C is −21.33°. Gas chromatography analysis indicated better than 99% pure major component.

EXAMPLE 7

Using the general method outlined in Example 1, 0.02 mole of 1,2:5,6-di-O-isopropylidene-D-glucofuranose in 1,4-dioxane was reacted with 0.0225 mole of 2-(2-chloroethyl)-N-methylpyrrolidine hydrochloride and 0.0675 mole of sodium hydroxide. After 18 hours the solvent was removed and the resulting orange oil was vacuum distilled under nitrogen. The residue consisted of the desired product, 1,2:5,6-di-O-isopropylidene-3-O-2'-{2''-(N''-methyl)-pyrrolidyl}-ethyl-D-glucofuranose having an optical rotation of $\{\alpha\}_D^{25} = -22.95°$ in chloroform.

EXAMPLE 8

1,2:5,6-di-O-isopropylidene-D-glucofuranose (0.1 mole) and N-(2-chloroethyl)-pyrrolidine hydrochloride (0.15 mole) are mechanically stirred and refluxed with 0.45 mole of sodium hydroxide in 150 ml of tetrahydrofuran for 18 hours. The tetrahydrofuran is removed from the reaction products and the resulting oil is vacuum distilled under nitrogen. The 3-O-2'-{N'-pyrrolidyl}-ethyl }-1,2:5,6-di-O-isopropylidene-D-glucofuranose derivative has a boiling point of 165°–171° C/0.15 mm Hg. Gas chromatography indicates a purity of 99%. Using the hydrolysis procedure outlined in Example 1, 10 g of the blocked oil was hydrolyzed and lyophillized giving a white hygroscopic crystalline solid.

EXAMPLE 9

The N',N'-dimethylamino-n-pentyl derivative of 1,2:5,6-di-O-isopropylidene-D-glucofuranose is made by condensing N,N-dimethylamino-n-pentyl-5-chloride hydrochloride with 1,2:5,6-di-O-isopropylidene-D-glucofuranose in the presence of pulverized sodium hydroxide in freshly purified, dry 1,4-dioxane as described in procedure in Example 1. The product was confirmed by gas chromatography and infrared spectra.

N,N-dimethylamino-n-pentyl chloride hydrochloride is made from commercially available sample of N,N-dimethylamino-n-pentyl alcohol by treatment with thionyl chloride ($SOCl_2$). Specifically, 10.7 g of thionyl chloride in a 250 ml three neck round bottom flask is cooled in a salt-ice water bath and stirred vigorously. To the cooled solution is added, dropwise, 10 g of N,N-dimethylamino-n-pentyl alcohol. The reaction is exothermic and temperature is carefully controlled. The mixture is stirred for one hour after the evolution of $SO_2$ and HCl subsides. The mixture is brought to room temperature and allowed to stir overnight. Absolute alcohol is added to destroy excess thionyl chloride. Ten grams of crude N,N-dimethylamino-n-pentyl chloride hydrochloride is obtained as a white solid. This is used directly for the condensation reaction with 1,2:5,6-di-O-isopropylidene-D-glucofuranose without further purification. The alcohol and chloride can be resolved on Chromosorb 103 gas chromtography column.

EXAMPLE 11

Well established methodology of prior art was employed to determine the antiviral potency of derivatives of 1,2-O-isopropylidene-D-glucofuranose·HCl against poliovirus, type 1, and rhinovirus, type 1A, in tissue culture at 37° C, employing HeLa cells with an agar overlay and WI-38 cell respectively. (See Wallis, C., F. Morales, J. Powell, and J. L. Melnick, Plaque enhancement of enteroviruses by magnesium chloride, cysteine, and pancreatin. J. Bacteriol. 91:1932-1935, 1966.) Poliovirus cell injury was determined by the study of plaque formation and rhinovirus was examined for cytopathic effect. In Table I, the virus inhibiting effects of three concentrations of the 3-O-3'-(N',N'-dimethylamino-n-propyl) derivative are depicted. The results are given as the degree of inhibition of infectivity, identified as plaque formation in the poliovirus system and as cytopathic effect in the system studying rhinovirus. Our results indicate that, at the appropriate dose, drug can completely inhibit 1000 plaque forming units (PFU) of poliovirus and a 1000 $TCID_{50}$ dose of rhinovirus 1A, a virus dose 1000 times that amount required to kill 50% of the tissue cultured cells.

TABLE I

DERIVATIVES OF 1,2-O-ISOPROPYLIDENE-D-GLUCOFURANOSE . HCl
SUMMARY OF ANTIVIRAL ACTIONS IN TISSUE CULTURE

| Derivative | Dose | System | Virus Type | Titer | Determination | Drug Effect |
|---|---|---|---|---|---|---|
| 3-O-3'-(N',N'-dimethylamino-n-propyl) | 1 μg/ml | HeLa cells in vitro with agar overlay | Poliovirus type 1 | 50 PFU[1] | Plaque number | Total inhibition |
| " | 20 μg/ml | " | " | 250 PFU | " | " |
| " | 40 μg/ml | " | " | 1000 PFU | " | " |
| 3-O-3'-(N',N'-dimethylamino-n-propyl) | 2 μg/ml | WI-38 cells | Rhinovirus type 1A | 100 $TCID_{50}$[2] | Cytopathic effect | Total inhibition |
| " | 20 μg/ml | " | " | 1000 $TCID_{50}$ | " | " |
| " | 40 μg/ml | " | " | 1000 $TCID_{50}$ | " | " |

[1] plaque-forming units.
[2] tissue culture infectious dose involving 50% of cells.

EXAMPLE 10

Bromine (9.8 g) was added slowly and dropwise to a mechanically stirred mixture of 50 g cracked ice and a chilled aqueous sodium hydroxide solution (7 g/20 ml water). After the addition of bromine is complete, 15 g of 1,2:5,6-di-O-isopropylidene-3-O-acetamido-D-glucofuranose (prepared by the general procedure outlined in Example 1 by the condensation of 1,2:5,6-di-O-isopropylidene-D-glucofuranose with 2-chloroacetamide in the presence of sodium hydroxide) is added in four portions 15 minutes apart. The reaction mixture is heated for one hour in a water bath. After this time an additional aqueous solution of sodium hydroxide (20 g/20 ml) is added and heating is continued for another hour. The mixture is cooled and extracted three times with ether. The ether extract is dried over anhydrous magnesium sulfate. The yellow hygroscopic solid remaining after evaporating off the ether is the desired 1,2:5,6-di-O-isopropylidene-3-O-aminomethyl-D-glucofuranose derivative. The product was identified by the disappearance of the carbonyl stretching at 1670 $cm^{-1}$ found in the parent acetamido compound.

EXAMPLE 12

Derivatives of 1,2-O-isopropylidene-D-glucofuranose hydrochloride were examined for their capacity to suppress influenza A 2 disease in mice and for their capacity to suppress death and nonlethal nervous system disease produced by the encephalomyocarditis virus in mice. In these studies, drug effect on lung pathology produced by a 15 $ID_{50}$ dose of influenza virus was examined. This dose is 15 times the dose that produces disease in 50% of the animals. Disease and drug effect on disease were determined by lung weight increase and reduction thereof. In the encephalomyocarditis study, 10 times the dose capable of killing 50% of the animals was given, and the degree of nonlethal disease and death were determined, as well as drug inhibition of both of these parameters. The results for these experiments are summarized in Table II, and indicate the production of significant reduction in lung weight increase by drug, as well as a significant inhibition of death and nonlethal disease produced by encephalomyocarditis virus. These effects were more potent for the 3-O-3'-(N',N'-dimethylamino-n-propyl) derivative than for the other two derivatives studied.

TABLE II

DERIVATIVES OF 1,2-O-ISOPROPYLIDENE-D-GLUCOFURANOSE . HCl
SUMMARY OF ANTIVIRAL ACTIONS IN VIVO IN MICE

| Derivative | Dose | System | Virus Type | Titer | Determination | Drug Effect |
|---|---|---|---|---|---|---|
| 3-O-3'-(N',N'-dimethylamino-n-propyl) | 20 mg/Kg | Mouse in vivo | Influenza type A | 15 $ID_{50}$[1] | Lung weight increase | Significant reduction in lung weight increase |
| 3-O-3'-(N',N'-dimethylamino-n-propyl) | 80 mg/Kg | Mouse in vivo | Encephalomyocarditis | 10 $LD_{50}$[2] | Involvement of CNS[3] and death | Significant inhibition of death and nonlethal disease |
| " | 160 mg/Kg | " | " | " | " | " |
| 3-O-2'-(N',N'-dimethylamino-iso-propyl) | 80 mg/Kg | " | " | " | " | inhibition significant, but less than n-propyl derivative |
| " | 160 mg/Kg | " | " | " | " | " |
| 3-O-3'-(2',N'-N'-trimethylamino-n-propyl) | 80 mg/Kg | " | " | " | " | " |
| " | 160 mg/Kg | " | " | " | " | " |

[1]infectious dose involving 50% of animals.
[2]lethal dose killing 50% of animals.
[3]central nervous system.

EXAMPLE 13

This example illustrates the preparation of 1,2:5,6-di-O-isopropylidene-3-O-2'-(N',N'-trimethylamino-n-propyl)-D-glucofuranose.

To 104 g (0.4 mole) of 1,2:5,6-di-O-isopropylidene-D-glucofuranose were added 0.6 mole of 3-chloro-N,N-2-trimethylpropylamine chloride hydrochloride, 1.8 moles prebaked sodium hydroxide beads, 10 g of anhydrous magnesium sulfate, and 500 ml of dry 1,4-dioxane in a 3-necked 3 liter reaction flask fitted with a mechanical stirrer and a reflux condenser. The reaction mixture was stirred vigorously and refluxed for about 20 hours. The progress of the reaction was monitored by gas chromatographic analysis. The reaction mixture was allowed to cool then filtered, and the dioxane solvent and unreacted amine were removed from the filtrate under reduced pressure with a rotary evaporator. A colorless to slightly yellow viscous oil (135 g) was obtained on fractional distillation at 144°–146° C at a pressure of 0.6 mm Hg. The oil had an optical rotation of $[\alpha]_o^{20}$ neat, 100 mm HG = $-20.05°$. The yield was more than 85%.

EXAMPLE 14

This example illustrates the preparation of 1,2:5,6-di-O-isopropylidene-3-O-3'-propanol-D-glucofuranose.

To a 3-necked reaction flask fitted with a mechanical stirrer and a reflux condenser were added 52 g of 1,2:5,6-di-O-isopropylidene-D-glucofuranose, 25 g of 3-chloropropanol, 24 g of sodium hydroxide, 5 g of anhydrous calcium chloride and 250–300 ml of dry 1,4-dioxane. The reaction mixture was gently refluxed for 16 to 20 hours and was monitored by gas chromatography. The solvent and unreacted 3-chloropropanol was removed by fractional distillation. The yield was more than 70%.

A similar reaction was run in an autoclave under steam pressure. The yield was lower and deep brown-red impurities were formed which were difficult to isolate by chemical steps or column chromatography.

EXAMPLE 15

This example illustrates the preparation of 1,2:5,6-di-O-isopropylidene-3-O-methylthiomethyl-D-glucofuranose.

A reaction mixture containing 52 g of 1,2:5,6-di-O-isopropylidene-D-glucofuranose, 58 g of chloromethylmethylsulfide, 48 g of baked sodium hydroxide and 200 ml of dry tetrahydrofuran was refluxed overnight with efficient mechanical stirring. The mixture was filtered, then dried and the solvent was removed under reduced pressure. On fractional distillation, the fraction boiling between 140° C and 148° C at 0.1 mm Hg pressure was collected as a yellowish oil. The oil also contained some unreacted 1,2:5,6-di-O-isopropylidene-D-glucofuranose. The latter was removed by selective crystallization from hot hexane solution. The final product was a yellow oil having an optical rotation of $[\alpha]°$ neat, 100 mm HG = $-42.5°$.

EXAMPLE 16

A solution of 26.0 g of 1,2:3,4-di-O-isopropylidene-D-galactopyranose in 50 ml of anhydrous THF was mixed with a suspension of 0.3 mole of 3-chloro-N,N-dimethylamino propane hydrochloride and 36 g of sodium hydroxide in 100 ml THF. The mixture was stirred vigorously and refluxed for three hours. The resulting brownish solution was cooled, filtered and most of the solvent was evaporated leaving a brown oil. The remaining solvent and unreacted 3-chloro-N,N-dimethylamino propane were removed by fractional distillation under reduced pressure. The residual oil was extracted with chloroform, decolorized with activated charcoal and dried over anhydrous magnesium sulfate. Removal of the chloroform solvent yielded 13.4 g of yellow oil, which was identified as 1,2:3,4-di-O-isopropylidene-6-O-3'-(N',N'-dimethylamino-n-propyl)-D-galactopyranose. Infrared and gas chromatography in accordance with Example 1 indicated the presence of one major component having a refractive index of $\eta_D^{28}$ = 1.461 and an optical rotation of $\{\alpha\alpha\}_D^{25}$ = $-49.40$ in chloroform.

The oil was refluxed with 50 ml of 0.5 N sulfuric acid for 18 hours. The resulting solution was washed with chloroform and the pH value was adjusted to 4.2. On lyophillization, the aqueous solution yielded 4.67 g of white crystalline solid 6-O-3'-(N',N'-dimethylamino-n-propyl)-D-galactopyranose having an optical rotation of $[\alpha]_D^{25}$ = $+77.2°$ in $H_2O$. A gas chromatography analysis in accordance with Example 1 indicated that the purity of the product was in excess of 95%.

EXAMPLE 17

This example illustrates the preparation of 6-O-2'-(N',N'-dimethylaminopropyl)-D-galactose.

The general procedure of Example 2 was followed with the exception of using 2-chloro-N,N-dimethylaminopropane hydrochloride as a starting material rather than the corresponding 3-chloro derivative. The intermediate product had an optical rotation in water of $[\alpha]_D^{24} = -54.5°$, and a refractive index of $n_D^{24} = 1.4552$. The final product had a rate of flow value on thin layer chromatography analysis in accordance with Example 1 of $R_f = 0.376$.

EXAMPLE 18

The most potent of the above derivatives, 3-O-3'-(N',N'-dimethylamino-n-propyl)-glucose was examined for its capacity to suppress influenza $A_2$/Hong Kong disease in mice. In this study mice were infected by a sublethal, disease-producing dose of mouse-adapted human influenza virus and were treated either with distilled water (control) or with 40 mg/kg compound. Fifty percent of the administered drug was in a form reduced in hydrophilicity by addition of the labile organic group acetone to the 1,2- positions to promote absorption into cells and slow release from body fat. Medication was administered orally, beginning 24 hours post-infection. Disease progression and drug effect were evaluated at 8 days by examination of the lung for pneumonic consolidation, after the method of T. W. Chang and L. Weinstein (Am. J. Med. Sci., 1973, in press) and by the objective technic of weighing the lungs. Note that lung weight increase during influenza infection reflects edema, hemorrhage and virus content (see P. Gordon and E. R. Brown, Canad. J. Micro. 18:1463, 1972). Below in Table 3, part A, we present the objective data for lung weights illustrating an 82% suppression of disease by our derivative.

The above medication was also examined for its capacity to prevent death in mice ill with a lethal influenza A/PR/8 infection. My drug was given subcutaneously at 3 dose levels, once 90 minutes before infection. The results illustrate a significant dose-dependent protection against death and are shown in Table 3, part B.

TABLE 3

A. ACTION IN MICE ILL WITH INFLUENZA $A_2$/HONG KONG DISEASE

| Group | Average Lung Weight (mg) | % Disease Suppression | Frequency of Normal Lungs (>170 mg) |
|---|---|---|---|
| Normal | 160 | | 21/21 |
| Infected control | 258 | | 1/21 |
| Infected treated | 177 | 82 | 13/21 |

B. ACTION IN MICE ILL WITH A LETHAL INFLUENZA A/PR/8 INFECTION

| Drug | Mortality Frequency at 8 days | % Mortality | % of Population Protected |
|---|---|---|---|
| 0 (Control) | 42/44 | 95 | |
| 10 mg/Kg | 18/22 | 81 | 14 |
| 40 mg/Kg | 16/22 | 72 | 23 |
| 160 mg/Kg | 10/22 | 45 | 50 |

EXAMPLE 19

Well established methodology of prior art was employed to determine the antiviral potency of compounds against influenza $A_2$ virus, Hong Kong strain, in tissue culture, employing the baby hamster kidney cell line (see R. L. Muldoon, L. Mezny and G. G. Jackson in Antimicrobial Agents and Chemotherapy 2:224-228, 1972). Virus infectivity was evaluated by both hemagglutination techniques and cytopathogenic effects, with identical results for each method. In Table 4 below the virus-inhibiting effects of two low drug concentrations, 3 and 10 μg/ml, are depicted. Results are given as the log decrease in infectivity of the virus inoculum. A log decrease of 4.0 is the maximum obtainable, representing complete suppression of virus growth in our system. The virus inoculum of day 0 was always 100 times that amount required to kill 50% of the tissue culture cells (100 $TCD_{50}$). These results indicate that different derivatives suppress viral growth by from 3 to 10,000 fold, the most potent effect being exerted by 3-O-3'-(N',N'-dimethylamino-n-propyl)-glucose.

TABLE 4

| Compound | Log Decrease in Infectivity of Virus Inoculum at Concentration of | |
|---|---|---|
| | 3 μg/ml | 10 μg/ml |
| 3-O-3'-(N',N'-dimethylamino-n-propyl)-D-glucose | 3.2 | 4.0 (max.) |
| 3-O-4'-(N-methylpiperidyl)-D-glucose | 2.5 | 3.5 |
| 3-O-2'-(N',N'-dimethylaminoethyl)-D-glucose | 2.5 | 3.5 |
| 3-O-3'-(2'-N',N'-trimethylamino-n-propyl)-D-glucose | 2.4 | 3.0 |
| α-N,N-dimethylaminoisopropyl glucoside | 1.5 | 2.5 |
| 6-O-3'-(N'-N'-dimethylamino-n-propyl)-D-galactose | 1.0 | 2.0 |
| 3-O-2'-(N',N'-dimethylaminopropyl)-D-glucose | 1.0 | 2.0 |
| 3-O-2'-(N',N'-dimethylaminoethyl)-D-glucose | 0.5 | 1.0 |
| 6-O-2'-(N',N'-dimethylaminopropyl)-D-galactose | 0.1 | 0.5 |

We claim:

1. In a method of preparing an ethereally substituted monosaccharide comprising the step of reacting
   1. a monosaccharide derivative having the general formula A-O-H, wherein O is oxygen, H is hydrogen and A is the residue of a monosaccharide selected from the group consisting of pentoses, hexoses and heptoses which has been derivatized with at least one substance selected from the group consisting of (1-a) at least one alcohol containing 1-18 carbon atoms to produce an acetal group at the site of at least one available hydroxyl residue, (1-b) at least one aldehyde containing 1-18 carbon atoms to produce at least one acetal group at the site of at least one available hydroxyl residue, (1-c) at least one ketone containing 1-18 carbon atoms to produce at least one ketal group at the site of at least one available hydroxyl residue, and (1-d) at least one organic acid residue containing 1-18 carbon atoms to produce an ester group at the site of at least one available hydroxyl residue, the said hydrolyzable acetal groups (1-a) and (1-b), ketal group (1-c) and ester group (1-d) being removable from said A by hydrolysis in an acidic aqueous medium having a pH value less than 7,
   2. an organic halide having the general formula Y-X, wherein X is selected from the group consisting of chlorine, bromine and iodine and Y is selected from the group consisting of (2-a) cyclic monovalent nitrogen containing organic radicals and residua free of carbonyl oxygen and (2-b) monovalent organic radicals and residua having the general formula —R₁—B, wherein B is selected from the group consisting of

—O—R₄ and —S—R₄, R₁ is a divalent organic radical having a linear carbon chain length of about 1–7 carbon atoms, R₂ and R₃ are selected from the group consisting of —H, —OH, —SH, halogen and monovalent organic radicals and residua having a linear carbon chain length of about 1–7 carbon atoms, R₄ is selected from the group consisting of —H and monovalent organic radicals and residua having a linear carbon chain length of about 1–7 carbon atoms, N is nitrogen, O is oxygen, S is sulphur and H is hydrogen, the said hydrogen atom H of the monosaccharide derivative A-O-H and the said halogen atom X of the organic halide being reactive whereby the said H is replaced by Y to produce an ethereally substituted monosaccharide derivative having the general formula A-O-Y wherein A and Y are as above defined, the improvement which comprises reacting said monosaccharide derivative (1) and the said organic halide (2) at an elevated reaction temperature below the thermal decomposition temperature thereof while dissolved in an anhydrous organic solvent in the present of a solid anhydrous strong inorganic base of a metal selected from the group consisting of the alkali metals and the alkaline earth metals and in the presence of a dehydrating agent which is a scavenger for water whereby anhydrous reaction conditions are maintained throughout the reaction.

2. The method of claim 1 wherein the dehydrating agent is anhydrous calcium chloride.

3. The method of claim 1 wherein the organic solvent is selected from the group consisting of 1,4-dioxane and tetrahydrofuran.

4. The method of claim 1 wherein the said inorganic base is selected from the group consisting of the anhydrous oxides and hydroxides of sodium, potassium and calcium.

5. The method of claim 1 wherein Y is

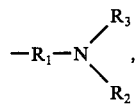

R₁ is a hydrocarbon radical having a linear carbon chain length of 1–3 carbon atoms, and R₂ and R₃ are selected from the group consisting of hydrogen and hydrocarbon radicals having a linear carbon chain length of 1–3 carbon atoms.

6. The method of claim 1 wherein Y is -(N',N'-dimethylamino-n-propyl).

7. In a method of preparing an ethereally substituted monosaccharide comprising the steps of reacting 1. a monosaccharide derivative having the general formula A₁-O-H, wherein O is oxygen, H is hydrogen and A₁ is the residue of a monosaccharide selected from the group consisting of pentoses, hexoses and heptoses which has been derivatized with at least one substance selected from the group consisting of (1-a) at least one alcohol containing 1–18 carbon atoms to produce a hydrolyzable acetal group at the site of at least one available hydroxyl residue, (1-b) at least one aldehyde containing 1–18 carbon atoms to produce at least one hydrolyzable acetal group at the site of at least one available hydroxyl residue, (1-c) at least one ketone containing 1–18 carbon atoms to produce at least one hydrolyzable ketal group at the site of at least one available hydroxyl residue, and (1-d) at least one organic acid residue containing 1–18 carbon atoms to produce a hydrolyzable ester group at the site of at least one available hydroxyl residue, the said hydrolyzable acetal groups (1-a) and (1-b), ketal group (1-c) and ester group (1-d) being removable from said A₁ by hydrolysis in an acidic aqueous medium having a pH value less than 7, with 2. an organic halide having the general formula Y-X, wherein X is a halogen atom selected from the group consisting of chlorine, bromine and iodine and Y is selected from the group consisting of (2-a) cyclic monovalent nitrogen containing organic radicals and residua free of carbonyl oxygen, and (2-b) monovalent organic radicals and residua having the general formula —R₁—B, wherein B is selected from the group consisting of

—O—R₄ and —S—R₄, R₁ is a divalent organic radical having a linear carbon chain length of about 1–7 carbon atoms, R₂ and R₃ are selected from the group consisting of —H,—OH, —SH, halogen and monovalent organic radicals and residua having a linear carbon chain length of about 1–7 carbon atoms, R₄ is selected from the group consisting of —H and monovalent organic radicals and residua having a linear carbon chain length of about 1–7 carbon atoms, N is nitrogen, O is oxygen, S is sulfur and H is hydrogen, the said hydrogen atom H of the monosaccharide derivative A₁-O-H and the said halogen atom X of the organic halide being reactive whereby the said H is replaced by Y to produce an ethereally substituted monosaccharide derivative having the general formula A₁-O-Y wherein A₁, Y and O are as above defined, the improvement which comprises reacting said monosaccharide derivative (1) and the said organic halide (2) at an elevated reaction temperature below the thermal decomposition thereof while dissolved in an anhydrous organic solvent in the presence of a solid anhydrous strong inorganic base of a metal selected from the group consisting of the alkali metals and the alkaline earth metals, separating the said ethereally substituted monosaccharide derivative having the general formula A₁-O-Y from the reaction mixture, and removing at least one but not all of said acetal, ketal or ester groups from A₁ by partial hydrolysis in an acidic aqueous medium having a pH value of about 3–6 to produce an ethereally substituted monosaccharide having the general formula A₂-O-Y, wherein O and Y are as above defined and A₂ is the residue of a monosaccharide corresponding to A₁ as above defined with at least one but not all of said acetal, ketal or ester groups being removed therefrom.

8. The method of claim 7 wherein the said monosaccharide derivative (1) is selected from the group consisting of glucose derivatives and galactose derivatives.

9. The method of claim 7 wherein the said monosaccharide derivative (1) is 1,2:5,6-di-O-isopropylidene D-glucofuranose.

10. The method of claim 9 wherein Y is

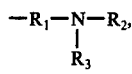

$R_1$ is a hydrocarbon radical having a linear carbon chain length of 1-3 carbon atoms, and $R_2$ and $R_3$ are selected from the group consisting of hydrogen and hydrocarbon radicals having a linear carbon chain length of 1-3 carbon atoms.

11. The method of claim 9 wherein Y is selected from the group consisting of
-(n-propylamino),
(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

12. The method of claim 9 wherein Y is -(N',N'-dimethylamino-n-propyl).

13. The method of claim 1 wherein the said monosaccharide derivative (1) has a general formula selected from the group consisting of:

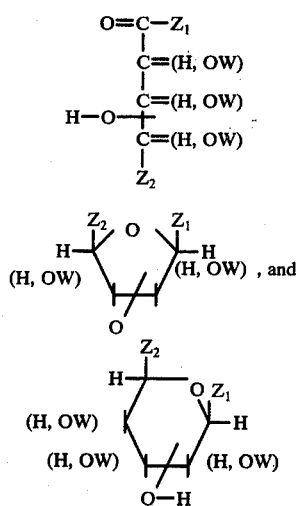

wherein $Z_1$ and $Z_2$ are selected from the group consisting of —H, —OH, and monovalent hydroxyalkyl, alkoxyl and alkoxyalkyl radicals containing up to 3 carbon atoms, W is selected from the group consisting of H and monovalent alkyl, alkenyl, cyclic alkane, cyclic aromatic, and acyl radicals containing 1-18 carbon atoms, and at least one $Z_1$, $Z_2$ or W is other than —H or —OH
the said monosaccharide derivative (1) being selected from the group consisting of glucose derivatives and galactose derivatives, the said glucose derivatives being derivatized in all —OH positions with the exception of the 1-O- or 3-O-position and the said galactose derivatives being derivatized in all —OH positions with the exception of the 6-O position whereby the glucose is ethereally monosubstituted in the 1-O- or 3-O-position and the galactose is ethereally monosubstituted in the 6-O- position, and Y is selected from the group consisting of
-(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

14. The method of claim 1 wherein the said monosaccharide derivative (1) is 1,2:5,6-di-O-isopropylidene-D-glucofuranose and Y is -(N',N'-dimethylamino-n-propyl).

15. The method of claim 7 wherein the said monosaccharide derivative (1) is selected from the group consisting of glucose derivatives and galactose derivatives, and
the glucose derivatives being derivatized in all —OH positions with the exception of the 1-O- or 3-O-positions and the galactose derivatives being derivatized in all —OH positions with the exception of the 6-O- position whereby the glucose is ethereally monosubstituted in the 1-O- or 3-O- position and the galactose is ethereally monosubstituted in the 6-O- position.

16. The method of claim 7 wherein the said monosaccharide derivative (1) is 1,2:5,6-di-O-isopropylidene-D-glucofuranose and Y is -(N',N'-dimethylamino-n-propyl), and
the hydrolysis is performed in a substantially non-oxidizing acidic aqueous medium having a pH value of about 3-6 to remove only one of the said isopropylidene groups.

17. The method of claim 1 wherein the said organic halide (2) is an amine, and the said amine is initially present in the form of a salt thereof.

18. The method of claim 1 wherein the said ethereally substituted monosaccharide derivative having the general formula A-O-Y is hydrolyzed to remove at least one of said hydrolyzable acetal, ketal or ester groups from A by hydrolysis in an acidic aqueous medium having a pH value less than 7 to produce an ethereally substituted monosaccharide having the general formula $A_3$-O-Y, wherein O and Y are as above defined and $A_3$ is a residue of a monosaccharide corresponding to A as above defined with at least one of said hydrolyzable acetal, ketal or ester groups being removed therefrom.

19. The method of claim 18 wherein the said hydrolysis is performed in a substantially non-oxidizing acidic aqueous medium having a pH value less than 3 to remove all of the said hydrolyzable acetal, ketal or ester groups from A.

20. The method of claim 7 wherein the said organic halide (2) is an amine, and the said amine is initially present in the form of a salt thereof.

* * * * *